(12) United States Patent
Kolosov et al.

(10) Patent No.: US 7,721,590 B2
(45) Date of Patent: May 25, 2010

(54) RESONATOR SENSOR ASSEMBLY

(75) Inventors: Oleg Kolosov, San Jose, CA (US);
Leonid Matsiev, San Jose, CA (US);
John F. Varni, Los Gatos, CA (US); **G.
Cameron Dales**, Saratoga, CA (US);
Olaf Ludtke, Vollersode-Wallhofen
(DE); Dirk Wullner, Lippstadt (DE);
Andreas Buhrdorf, Bremen (DE);
Heiko Dobrinski, Bremen (DE)

(73) Assignees: Meas France, Toulouse (FR); Hella KGAA Hueck & Co., Lippstadt (DE)

( * ) Notice: Subject to any disclaimer, the term of this patent is extended or adjusted under 35 U.S.C. 154(b) by 702 days.

(21) Appl. No.: 10/550,075

(22) PCT Filed: Mar. 19, 2004

(86) PCT No.: PCT/US2004/008552

§ 371 (c)(1),
(2), (4) Date: Nov. 22, 2006

(87) PCT Pub. No.: WO2004/086003

PCT Pub. Date: Oct. 7, 2004

(65) Prior Publication Data
US 2007/0052970 A1    Mar. 8, 2007

Related U.S. Application Data

(60) Provisional application No. 60/456,517, filed on Mar. 21, 2003.

(51) Int. Cl.
*G01N 11/16* (2006.01)

(52) U.S. Cl. .................................... 73/54.41; 73/53.05
(58) Field of Classification Search ................ 73/24.05, 73/30.01, 32 A, 54.24, 54.26, 54.41, 32 R
See application file for complete search history.

(56) References Cited

U.S. PATENT DOCUMENTS 3,273,377 A    9/1966    Testerman et al.

(Continued)

FOREIGN PATENT DOCUMENTS

DE    4424422 A1    7/1994

(Continued)

OTHER PUBLICATIONS

A&D Weighing, SV Series Users' Handbook V1.04E.

(Continued)

*Primary Examiner*—John Fitzgerald
(74) *Attorney, Agent, or Firm*—Howard IP Law Group, PC (57) ABSTRACT

An improved method and assembly, wherein the method generally includes the steps of providing a coated or uncoated sensor element having an exposed sensing surface; attaching the sensor element to a platform so that the exposed sensing surface is spaced from the platform; and optionally applying a protective layer over the platform while maintaining the sensing surface as exposed. The assembly includes a resonator having a free portion with a sensing surface is incorporated onto a platform, components of the sensor are physically shielded from harsh operating conditions, the requisite space is maintained between the free portion of the resonator and the platform, and the sensing surface of the resonator remains exposed for sensing.

20 Claims, 4 Drawing Sheets

U.S. PATENT DOCUMENTS

| | | |
|---|---|---|
| 3,622,968 A | 11/1971 | Silverman |
| 3,710,275 A | 1/1973 | King |
| 3,718,032 A | 2/1973 | Gray |
| 3,762,197 A | 10/1973 | Roof et al. |
| 3,778,757 A | 12/1973 | Houston |
| 3,902,365 A | 9/1975 | Knauth |
| 3,903,732 A | 9/1975 | Rork et al. |
| 3,921,622 A | 11/1975 | Cole et al. |
| 3,926,271 A | 12/1975 | Patashnick |
| 4,103,224 A | 7/1978 | Taro et al. |
| 4,145,922 A | 3/1979 | Estrada et al. |
| 4,312,228 A | 1/1982 | Wohltjen |
| 4,342,936 A | 8/1982 | Marcus et al. |
| 4,349,881 A | 9/1982 | November et al. |
| 4,361,026 A | 11/1982 | Muller et al. |
| 4,370,662 A | 1/1983 | Hou et al. |
| 4,391,338 A | 7/1983 | Patashnick et al. |
| 4,526,480 A | 7/1985 | Ward |
| 4,535,620 A | 8/1985 | Cunningham |
| 4,543,829 A | 10/1985 | Lerch |
| 4,549,427 A | 10/1985 | Kolesar, Jr. |
| 4,596,697 A | 6/1986 | Ballato |
| 4,602,498 A * | 7/1986 | Glikberg et al. ............. 73/32 A |
| 4,602,505 A | 7/1986 | Kanda et al. |
| 4,624,129 A | 11/1986 | Haynes |
| 4,644,803 A | 2/1987 | Ward |
| 4,696,181 A | 9/1987 | Rapprecht et al. |
| 4,721,874 A | 1/1988 | Emmert |
| 4,729,237 A | 3/1988 | Suzuki et al. |
| 4,734,609 A | 3/1988 | Jasmine |
| 4,741,200 A | 5/1988 | Hammerle |
| 4,760,351 A | 7/1988 | Newell et al. |
| 4,767,719 A | 8/1988 | Finlan |
| 4,779,451 A | 10/1988 | Ezawa et al. |
| 4,782,332 A | 11/1988 | Cipris et al. |
| 4,783,987 A | 11/1988 | Hager et al. |
| 4,802,370 A | 2/1989 | EerNisse et al. |
| 4,802,384 A | 2/1989 | Schwarz et al. |
| 4,812,698 A | 3/1989 | Chida et al. |
| 4,862,384 A | 8/1989 | Bujard |
| 4,890,480 A | 1/1990 | Young |
| 4,893,496 A | 1/1990 | Bau et al. |
| 4,904,978 A | 2/1990 | Barth et al. |
| 4,910,523 A | 3/1990 | Huguenin et al. |
| 4,922,745 A | 5/1990 | Rudkin et al. |
| 4,945,634 A * | 8/1990 | Kumada ........ 29/854 |
| 4,970,492 A | 11/1990 | King |
| 5,006,845 A | 4/1991 | Calcar et al. |
| 5,037,779 A * | 8/1991 | Whalley et al. ............. 257/687 |
| 5,179,028 A | 1/1993 | Vali et al. |
| 5,191,791 A | 3/1993 | Gerardi et al. |
| 5,201,215 A | 4/1993 | Granstaff et al. |
| 5,204,529 A | 4/1993 | Diatschenko |
| 5,224,174 A | 6/1993 | Schneider et al. |
| 5,235,844 A | 8/1993 | Bonne et al. |
| 5,243,756 A * | 9/1993 | Hamburgen et al. .......... 29/841 |
| 5,253,530 A | 10/1993 | Letcher, III |
| 5,283,037 A | 2/1994 | Baer et al. |
| 5,296,374 A | 3/1994 | Culshaw et al. |
| 5,306,644 A | 4/1994 | Myerholtz et al. |
| 5,325,704 A | 7/1994 | Mariani et al. |
| 5,332,961 A | 7/1994 | Hammerle |
| 5,334,900 A | 8/1994 | Kawashima |
| 5,338,416 A | 8/1994 | Mlcak et al. |
| 5,357,964 A | 10/1994 | Spivey et al. |
| 5,361,632 A | 11/1994 | Magnani |
| 5,375,470 A | 12/1994 | Matsushima et al. |
| 5,405,808 A * | 4/1995 | Rostoker et al. ............. 29/841 |
| 5,421,190 A | 6/1995 | Brandle et al. |
| 5,434,650 A | 7/1995 | Nakahara et al. |
| 5,435,170 A | 7/1995 | Voelker et al. |
| 5,445,008 A | 8/1995 | Wachter et al. |
| 5,454,045 A | 9/1995 | Perkins et al. |
| 5,455,475 A | 10/1995 | Josse et al. |
| 5,464,509 A | 11/1995 | Mlcak et al. |
| 5,469,369 A | 11/1995 | Rose-Pehrsson et al. |
| 5,477,726 A | 12/1995 | Stabinger et al. |
| 5,488,866 A | 2/1996 | Ravel et al. |
| 5,524,477 A | 6/1996 | Wajid |
| 5,524,636 A | 6/1996 | Sarvazyan et al. |
| 5,531,091 A | 7/1996 | Gademann et al. |
| 5,533,402 A | 7/1996 | Sarvazyan et al. |
| 5,559,291 A * | 9/1996 | Hasegawa ............... 73/504.12 |
| 5,571,401 A | 11/1996 | Lewis et al. |
| 5,604,441 A | 2/1997 | Freese et al. |
| 5,610,335 A * | 3/1997 | Shaw et al. ............. 73/514.36 |
| 5,622,223 A | 4/1997 | Vasquez |
| 5,653,939 A | 8/1997 | Hollis et al. |
| 5,661,233 A | 8/1997 | Spates et al. |
| 5,670,709 A | 9/1997 | Gallagher |
| 5,693,884 A * | 12/1997 | Kato ..................... 73/514.33 |
| 5,698,089 A | 12/1997 | Lewis et al. |
| 5,705,399 A | 1/1998 | Larve |
| 5,734,098 A | 3/1998 | Kraus et al. |
| 5,741,961 A | 4/1998 | Martin et al. |
| 5,744,902 A | 4/1998 | Vig |
| 5,770,038 A | 6/1998 | Iwama |
| 5,776,359 A | 7/1998 | Schultz et al. |
| 5,777,210 A | 7/1998 | Voelker et al. |
| 5,789,665 A | 8/1998 | Voelker et al. |
| 5,792,938 A | 8/1998 | Gokhfeld |
| 5,798,452 A | 8/1998 | Martin et al. |
| 5,818,731 A | 10/1998 | Mittal et al. |
| 5,827,952 A | 10/1998 | Mansure et al. |
| 5,852,229 A | 12/1998 | Josse et al. |
| 5,877,411 A * | 3/1999 | Namerikawa et al. ...... 73/64.53 |
| 5,885,849 A | 3/1999 | DiStefano et al. |
| 5,889,351 A | 3/1999 | Okumura et al. |
| 5,915,499 A | 6/1999 | Few |
| 5,918,354 A | 7/1999 | Ikegami et al. |
| 5,959,247 A * | 9/1999 | Armstrong et al. .......... 174/528 |
| 5,959,297 A | 9/1999 | Weinberg et al. |
| 5,985,356 A | 11/1999 | Schultz et al. |
| 6,023,961 A | 2/2000 | Discenzo et al. |
| 6,034,775 A | 3/2000 | McFarland et al. |
| 6,041,642 A | 3/2000 | Duncan |
| 6,044,694 A | 4/2000 | Anderson et al. |
| 6,047,590 A * | 4/2000 | Namerikawa et al. ...... 73/54.24 |
| 6,082,894 A * | 7/2000 | Batko et al. .................. 374/142 |
| 6,126,311 A | 10/2000 | Schuh |
| 6,151,123 A | 11/2000 | Nielson |
| 6,155,098 A | 12/2000 | Shapiro et al. |
| 6,157,449 A | 12/2000 | Hajduk |
| 6,175,409 B1 | 1/2001 | Nielsen et al. |
| 6,176,131 B1 * | 1/2001 | Hecht et al. .............. 73/204.26 |
| 6,176,323 B1 | 1/2001 | Weirich et al. |
| 6,182,499 B1 | 2/2001 | McFarland et al. |
| 6,196,057 B1 * | 3/2001 | Discenzo .................. 73/54.01 |
| 6,223,589 B1 | 5/2001 | Dickert et al. |
| 6,231,811 B1 * | 5/2001 | Namerikawa et al. ...... 422/68.1 |
| 6,247,354 B1 | 6/2001 | Vig et al. |
| 6,260,407 B1 | 7/2001 | Petro et al. |
| 6,260,408 B1 | 7/2001 | Vig et al. |
| 6,265,226 B1 | 7/2001 | Petro et al. |
| 6,269,686 B1 | 8/2001 | Hahn et al. |
| 6,275,137 B1 | 8/2001 | Doppalapudi et al. |
| 6,286,363 B1 | 9/2001 | Discenzo |
| 6,294,388 B1 | 9/2001 | Petro |
| 6,296,771 B1 | 10/2001 | Miroslav |
| 6,306,358 B1 | 10/2001 | Yamamoto |
| 6,311,549 B1 | 11/2001 | Thundat et al. |
| 6,327,890 B1 | 12/2001 | Galipeau et al. |
| 6,336,353 B2 | 1/2002 | Matsiev et al. |
| 6,371,640 B1 | 4/2002 | Hajduk et al. |

| | | | |
|---|---|---|---|
| 6,389,690 B1 * | 5/2002 | McCullough et al. ......... 29/840 | |
| 6,393,895 B1 | 5/2002 | Matsiev et al. | |
| 6,401,519 B1 | 6/2002 | McFarland et al. | |
| 6,406,632 B1 | 6/2002 | Safir | |
| 6,407,479 B1 | 6/2002 | Moellendorf et al. | |
| 6,412,131 B1 | 7/2002 | Zhao et al. | |
| 6,441,716 B1 | 8/2002 | Doppalapudi et al. | |
| 6,456,096 B1 | 9/2002 | Ericson et al. | |
| 6,459,995 B1 | 10/2002 | Collister | |
| 6,490,911 B1 * | 12/2002 | Namerikawa et al. ...... 73/54.24 | |
| 6,494,079 B1 | 12/2002 | Matsiev et al. | |
| 6,507,945 B1 | 1/2003 | Rust et al. | |
| 6,509,749 B1 | 1/2003 | Buelna et al. | |
| 6,511,915 B2 | 1/2003 | Mlcak | |
| 6,519,034 B1 | 2/2003 | Engler et al. | |
| 6,535,001 B1 | 3/2003 | Wang | |
| 6,536,259 B2 * | 3/2003 | Mattes ....................... 73/12.09 | |
| 6,536,634 B2 | 3/2003 | Berndorfer et al. | |
| 6,545,392 B2 | 4/2003 | Kawauchi et al. | |
| 6,557,396 B2 | 5/2003 | Ohki | |
| 6,564,126 B1 | 5/2003 | Lin et al. | |
| 6,575,020 B1 * | 6/2003 | de Charmoy Grey et al. ........................... 73/54.23 | |
| 6,626,025 B2 | 9/2003 | Potyrailo et al. | |
| 6,640,644 B1 | 11/2003 | Mireles et al. | |
| 6,644,095 B2 | 11/2003 | VanMullekom et al. | |
| 6,658,429 B2 | 12/2003 | Dorsett, Jr. | |
| 6,661,162 B1 | 12/2003 | Nagai et al. | |
| 6,664,067 B1 | 12/2003 | Hajduk et al. | |
| 6,928,877 B2 | 8/2005 | Carlson et al. | |
| 7,100,427 B2 * | 9/2006 | Kahn et al. .................. 73/53.01 | |
| 7,171,849 B2 * | 2/2007 | Kandler ....................... 73/146.5 | |
| 7,210,332 B2 * | 5/2007 | Kolosov et al. ............ 73/24.06 | |
| 7,254,990 B2 * | 8/2007 | Matsiev et al. ............. 73/54.41 | |
| 7,294,540 B2 * | 11/2007 | Lee et al. ..................... 438/172 | |
| 7,350,367 B2 * | 4/2008 | Matsiev et al. ................ 62/129 | |
| 2001/0010174 A1 | 8/2001 | Matsiev et al. | |
| 2002/0029900 A1 * | 3/2002 | Wimberger Friedl et al. ............................ 174/258 | |
| 2002/0064649 A1 | 5/2002 | Lembke et al. | |
| 2002/0068488 A1 | 6/2002 | Tuller et al. | |
| 2002/0070841 A1 | 6/2002 | Doppalapudi et al. | |
| 2002/0074897 A1 | 6/2002 | Ma et al. | |
| 2002/0092340 A1 | 7/2002 | Prater et al. | |
| 2002/0113596 A1 | 8/2002 | Horie et al. | |
| 2002/0121132 A1 | 9/2002 | Breed et al. | |
| 2002/0137348 A1 | 9/2002 | Mlcak | |
| 2002/0148529 A1 | 10/2002 | Berndorfer et al. | |
| 2002/0162385 A1 | 11/2002 | Ismail et al. | |
| 2002/0178787 A1 | 12/2002 | Matsiev et al. | |
| 2002/0178805 A1 | 12/2002 | DiFoggio et al. | |
| 2002/0194906 A1 | 12/2002 | Goodwin et al. | |
| 2003/0000291 A1 | 1/2003 | Kolosov et al. | |
| 2003/0041653 A1 | 3/2003 | Matsiev et al. | |
| 2003/0041659 A1 | 3/2003 | Marszlalek et al. | |
| 2003/0053516 A1 * | 3/2003 | Atherton ....................... 374/143 | |
| 2003/0062910 A1 | 4/2003 | Wang et al. | |
| 2003/0083825 A1 | 5/2003 | Berndorfer | |
| 2003/0116497 A1 | 6/2003 | Carlson et al. | |
| 2003/0118078 A1 | 6/2003 | Carlson et al. | |
| 2003/0119060 A1 | 6/2003 | Desrosiers et al. | |
| 2003/0233886 A1 * | 12/2003 | Uramachi et al. ......... 73/861.08 | |
| 2007/0245811 A1 * | 10/2007 | Discenzo ................... 73/53.05 | |

FOREIGN PATENT DOCUMENTS

| | | |
|---|---|---|
| DE | 10014724 A1 | 9/2001 |
| EP | 0282251 A3 | 9/1988 |
| EP | 0317356 B1 | 1/1993 |
| EP | 0282251 B2 | 2/1993 |
| EP | 0676638 A2 | 10/1995 |
| EP | 0769695 A2 | 4/1997 |
| EP | 0779510 A2 | 6/1997 |
| EP | 0813236 A1 | 12/1997 |
| GB | 2114745 | 8/1983 |
| GB | 2187286 | 9/1987 |
| JP | 59126931 | 7/1984 |
| JP | 60134617 | 7/1985 |
| JP | 402161323 | 6/1990 |
| JP | 5129874 | 5/1993 |
| JP | 8112613 | 5/1996 |
| JP | 11094726 | 4/1999 |
| WO | WO 9801739 A2 * | 1/1998 |

OTHER PUBLICATIONS

"Sensor Technology Improves Jet Engine Reliability", http://www.afrlhorizons.com/Briefs/June01/PR0003.html, Oct. 3, 2002.

"Combinatorial Chemistry—The Emperor's New Clothes?", Microporous and Mesoporous Materials, 2000.

"An in vitro urea sensor using a torsion-wave crystal device", Sensors and Actuators B,8 (1992) 143-149, 1992.

"Viscosity Sensor Based on a Symmetric Dual Quartz Thickness Shear Resonator" 2003 IEEE.

"Elemente der Angewandten Elektronik", Friedr. Vieweg & Sohn, Jan. 29, 2004.

"Micromachined Viscosity Sensor for Real-Time Polymerization Monitoring" Transducers '97, Jun. 1997.

"Resonance Response of Scanning Force Microscopy Cantilevers", 1994 American Institute of Physics, Aug. 1994.

"CJV-5000 Vibro Viscometer Utilizing Tuning-Fork Technology", Jun. 18, 2003.

"Fabrication of High Frequency Nanometer Scale Mechanical Resonators from Bulk Si Crystals", A. N. Cleland and M.L. Roukes, American Institute of Physics, Oct. 28, 1996.

Delphi, "Sensors and Actuators Intellek Oil Condition Sensor", 2002.

"Integrated On-Line Multisensing of Fluid Flow Using a Mechanical Resonator" Sensors and Actuators, 2000.

"On-Line Monitoring of the Viscosity in Dextran Fermentation Using Piezoelectric Quartz Crystal" Biotechnology and Bioengineering, vol. 36, pp. 636-641, 1990.

Electronic Devices "Epson presents the MC-30A: Reliable 32.768kHz Dedicated to Automotive Applications", Aug. 25, 2003.

"Viscoelastic Properties of Polymers" John D. Ferry, Third Edition, John Wiley & Sons, Inc., 1980.

"Field Trials of the Viscosity & Fluid Density Tool (VFD)" Nan Gall Technology, Aug. 2002.

"Improved Acoustic Viscosimeter Technique" M. R. Fisch, R. P. Moeller, and E. F. Carome, 1976.

"The Vibrating Tuning Fork Fluid Density Tool" by Alan Fleming.

"Sensors" Fraunhofer Verbund Mikroelektronik, Oct. 3, 2002.

"Smart Sensor System for Trace Organophosphorus and Organosulfur Vapor Detection Employing a Temperature-Controlled Array of Surface Acoustic Wave Sensors, Automated Sample Preconcentration, and Pattern Recognition", American Chemical Society, 1993.

"Measurement of Viscosity and Shear Wave Velocity of a Liquid or Slurry for On-Line Process Control", Ultrasonics 39 (2002) 623-630, 2002.

"On-Line Sensor for Density and Viscosity Measurements of a Liquid or Slurry for Process Control in the Food Industry", 2004.

"Development of Micro-Hydraulic Transducer Technology", Nesbitt W. Hagood et al.

"An Acoustic Automotive Engine Oil Quality Sensor", 1977 IEEE International Frequency Control Symposium, 1997.

"Sensor" J.M. Hammond, 1997.

"Ultrasonic Sensors for Process Monitoring and Chemical Analysis" State-of -the-Art and Trends Peter Hauptmann, 1998.

"Refrigerant Flow in Evaporators", OEM Products, Feb. 5, 2004.

"Applications of the Piezoelectric Crystal Detector in Analytical Chemistry", 1890 Analytical Chemistry, vol. 49, No. 13, Nov. 1977.

"Surface Acoustic Wave Hygrometer: Measuring Water Vapor in Earth's Atmosphere", http://mishkin.jpl.nasa.gov/spacemicro/MWS_PAPER, Mar. 6, 2002.

"SOS™ Smart Oil Sensor" Impact Technologies, LLC, 2003.

"Viscosity Sensing Using a Love-Wave Device", Sensors and Actuators A 68 (1998) 275-281, 1998.

"The Oscillation Frequency of a Quartz Resonator in Contact with a Liquid" IBM Research Laboratory, K33-281, 1985.

"Lecture Notes on Shear and Friction Force Detection with Quartz Tuning Forks" by Khaled Karrai, Mar. 2000.

"Network Analysis Method Applied to Liquid-Phase Acoustic Wave Sensors", 1990 American Chemical Society, 1990.

"Device for the Investigation of The Humidity-Related Behaviors of Materials", Department of Physics, 1986.

"Theory of the Vibrating Tuning Fork Fluid Density Tool", May 7, 2003.

"Fluid Mechanics" by L. D. Landau and E. M. Lifshitz, Addison-Wesley Publishing Company, Inc., 1959.

"Vibratory Process Control Transducers" by R. M. Langdon, Ph.D.

"A Remote Acoustic Engine Oil Quality Sensor" 1997 IEEE, 1997.

"Electromechanical Behavior of PZT—Brass Unimorphs", 1999.

"Operation of an Ultrasensitive 30-MHz Quartz Crystal Microbalance in Liquids" Anal. Chem. 1993, 65, 1545-1551, 1993.

"Two-Dimensional Micromechanical Bimorph Arrays for Detection of Thermal Radiation", American Institute of Physics, Jun. 17, 1997.

"Viscosity and Density Sensing with Ultrasonic Plate Waves", Sensors and Actuators, A21-A23, 1990.

"Measurement of the Viscosity and Shear Elasticity of Liquids by Means of a Torsionally Vibrating Crystal", by W. P. Mason, Murray Hill, N.J., Jan. 29, 2004.

"Application of Flexural Mechanical Resonators to Simultaneous Measurements of Liquid Density and Viscosity", L. F. Matsiev, 1998.

"Theory of Electoacoustics", McGraw-Hill International Book Company, 1981.

1 MHz Quartz Length Extension Resonator as a Probe for Scanning Near-Field Acoustic Microscopy, Thin Solid Films 264 (1995) 172-175, 1995.

A Quartz Crystal Viscosity Sensor for Monitoring Coagulation Reaction and its Application to a multichannel Coagulation Detector, Biosensors & Bioelectronics, 1991.

"Computation of Equivalent Circuit Parameters of Quartz Crystals in Contact with Liquids and Study of Liquid Properties", American Chemical Society, 1988.

"Viscosity Monitoring with a Piezoelectric Quartz Crystal and its Application to Determination of Endotoxin by Gelatin of Limulus Amebocyte Lysate", Elsevier Science Publishers B.V., 1988.

High Throughput Experimentation for the Synthesis of New Crystalline Microporous Solids, Microporous and Mesoporous Materials 48 (2001) 355-365.

"Electrolytic Determination of Nanomolar Concentrations of Silver in Solution with a Piezoelectric Quartz Crystal", Analytica Chimica Acta, 131 (1981) 97-102.

"Harsh Environment Fluid Viscosity-Density Sensor", http://www.fastlane.nsf.gov/servlet/showaward?award=0239151, Feb. 5, 2004.

"An Accurate Non-Radioactive Fluid Density Sensor", by Chris Nussbaum, Apr. 1, 2003.

"Viscous Drag Measurements Utilizing Microfabricated Cantilevers", American Institute of Physics, 1996.

"@ Kavlico . . . Our Sensors are the Solution", Capability Brochure Industrial Sensors and Transducers.

"The Lubri-Sensor Electronic Oil Quality Analyser", http://www.pmlubricants.com.au/pm_lube_concept/lubri-sensor.htm, Oct. 3, 2002.

"Processing and Characterization of Piezoelectric Materials and Integration into Microelectromechanical Systems", Annual Reviews, 1998.

"Reliable Ceramics for Advanced Heat Engines", American Ceramic Society Bulletin, vol. 74, No. 4, Apr. 1995.

"Hygroscopicity, Measurement, Apparatus".

"Frequency Response of Cantilever Beams Immersed in Viscous Fluids with Applications to the Atomic Force Microscope", Journal of Applied Physics, vol. 84, No. 1, Jul. 1, 1998.

"A New Method Based on Acoustic Impedance Measurements for Quartz Immunosensors", Sensors and Actuators B 43 (1997) 217-223.

"The Future of Pressure and Temperature Measurement", Senstronics Storm.

"Simultaneous Liquid Viscosity and Density Determination with Piezoelectric Unimorph Cantilevers", Journal of Applied Physics, vol. 89, No. 2, Jan. 15, 2001.

"Sinims Oil and Gas Workshop", ICMS, Edinburgh, Mar. 11, 2002.

"Water Sorption Isotherms and Enthalpies of Water Sorption by Lysozyme using the Quartz Crystal Microbalance/Heat Conduction Calorimeter", Biochimica et Biophysica Acta 1594 (2002) 150-159.

"A Vibrating Tuning Fork Fluid Density Tool", Smith Institute, Feb. 5, 2004.

"ViscoMaster HFO Viscosity Transmitter for Marine and Power Applications", Solartron Mobrey.

"Engine Oil Viscosity Sensors Using Disks of PZT Ceramic as Electormechanical Vibrators", SAE Technical Paper Series, May 8, 1997.

"Surface Acoustic Wave (SAW) Hygrometer (Micro Weather Station)", TAP: Gallery, Mar. 16, 2002.

"Preparation of Chemically Etched Piezoelectric Resonators for Density Meters and Viscometers", Mat. Res. Bull., vol. 22, pp. 1267-1274, 1987.

"Crimpen—eine ausgereifte Anschlubtechnik", F&M Elektromechanik.

"Evaluation of an Equivalent Circuit Model for Thickness-Shear Mode Resonators in Liquids", VTT, Chemical Technology, Polymer and Fibre Technology, Sep. 1996.

"Cantilever Sensor Research Tool for Science and Industry", diScentris, 2003.

"Multi-Function Microsensor for Oil Condition Monitoring Systems", AMAA.

"A Precise and Robust Quartz Sensor Based on Tuning Fork Technology for ($SF_6$)—Gas Density Control", Sensors and Actuators 80, 2000.

"Contributions of Amplitude Measurement in QCM Sensors", Chao Zhang and Guanping Feng, IEEE, 1996.

"Determination of Liquid Density with a Low Frequency Mechanical Sensor Based on Quartz Tuning Fork", Sensors and Actuators B 84, 2002.

U.S. Appl. No. 09/550,549 entitled "Automated Process Control and Data Management System and Methods" (Crevier et al.), Apr. 14, 2000.

"Oil Quality Sensor", Automotive Engineering International Online, http://www.sae.org/automag/top50prod/17.htm, Feb. 5, 2004, 1 pg.

* cited by examiner

RESONATOR SENSOR ASSEMBLY

CLAIM OF BENEFIT OF FILING DATE

The present application claims the benefit of the filing date of PCT Application Ser. No. PCT/US04/08552 (filed Mar. 19, 2004) (published as WO 04/086003) and U.S. Provisional Application Ser. No. 60/456,517 (filed Mar. 21, 2003), the contents of which are hereby incorporated by reference in their entirety.

TECHNICAL FIELD

The present invention relates generally to the assembly of sensing devices, and more particularly to the packaging of fluid condition sensors such as for the sensing of synthetic or natural petroleum fluids.

BACKGROUND

U.S. Provisional Application Ser. No. 60/419,404, (entitled "Machine Fluid Sensor and Method"; filed Oct. 18, 2002) (hereby incorporated by reference) discloses improved machine fluid sensors and methods. There is a need for the ability to package sensing devices so that they can withstand their operating conditions. Exemplary applications in which these sensors may be used in engines in general, automobiles, heavy machinery, military equipment, airplane parts, oil drilling, exploration and production well logging, oil refining, pipeline and quality control applications, marine transportation, sub-sea exploration and aerospace related equipment, or any other fluid containing application. In general, sensors for these applications will include very small components that need to be able to withstand harsh operating environment conditions. The ability to assemble such devices efficiently using automated materials handling equipment is also important.

SUMMARY OF THE INVENTION

In general, the present invention meets the above needs by providing an improved method that generally includes the steps of:

providing a coated or uncoated sensor element having an exposed sensing surface;
  attaching the sensor element to a platform so that the exposed sensing surface is spaced from the platform; and
  optionally applying a protective layer over the platform and/or sensor while maintaining the exposed sensing surface.

A highly preferred sensor of the present invention includes a resonator, and more preferably a tuning fork resonator.

Among other advantages, the present invention affords the ability to provide improved sensor assemblies for a number of different applications. The sensor assemblies of the present invention thus preferably include at least one and more preferably a combination of two or more of the following:

operates for long periods of time (e.g., at least 3 months, and more preferably at least 1 year or longer) over a temperature range of −40° C. to 170° C. and more preferably −60° C. to 300° C., without compromise to the material sensor performance characteristics;
  provides protection to fragile components that are typically small (e.g., smaller than 5 mm, and in some instances having a smallest dimension that is smaller than 1 mm), in harsh environments such as environments that include corrosive media, abrasive media, or combinations thereof;
  provides a packaged device that is compact (e.g., smaller than about 15 cm$^3$, having a footprint of less than about 40 cm$^2$, and more preferably smaller than about 10 cm$^3$, having a footprint of less than about 20 cm$^2$), which can be used alone or combined with other components, such as an application specific integrated circuit (ASIC) onto a common platform (e.g., a lead frame or the like);
  includes individual or modular components that can be readily handled by automated materials handling equipment, such as components including a flat surface for handling by "pick and place" robots; or
  includes structure that permits for calibration of the sensor against a material having a known characteristic or for initializing the sensor upon introduction of a new fluid.

Accordingly, it can be seen that the present invention provides a solution for a number of competing technological challenges; notably, for example, the preparation of an assembly in which a sensor having a free portion with a sensing surface is incorporated onto a platform, components of the sensor are physically shielded from harsh operating conditions, the requisite space is maintained between the free portion of the sensor and the platform, and the sensing surface of the sensor remains exposed for sensing.

DETAILED DESCRIPTION OF THE PREFERRED EMBODIMENTS

The present invention is predicated upon the discovery of methods for assembling a sensor that includes a sensing element that requires exposure over at least a portion of its outer surface to ambient conditions. More particularly, the present invention is predicated upon the discovery of methods for assembling a fluid sensor that includes a resonator sensing element that requires exposure over at least a portion of its outer surface to the fluid it is sensing.

One preferred method of the present invention generally includes the steps of:

providing a coated or uncoated sensor element having an exposed sensing surface;

attaching the sensor element to a platform so that the exposed sensing surface is spaced from the platform; and optionally applying a protective layer over the platform and/or sensor while maintaining the exposed sensing surface.

In a particularly preferred embodiment, which is illustrated herein by description of a tuning fork resonator as the sensing element, a coated or uncoated tuning fork resonator is provided and has tines that are free to resonate upon application of an input signal (e.g., a varying frequency input signal). The resonator is attached to a platform in a manner that maintains the tines spaced from the platform. Optionally, a protective layer is applied over the resonator (other than over the tines) and the platform. It should be appreciated that even though the present invention is illustrated with reference to a tuning fork resonator (e.g., having two, three or more tines), the invention is not so limited. For example, the features herein may be employed with respect to any of a number of types of sensors, including for example, cantilevers, unimorphs, bimorphs, membrane resonators, torsional resonators, or other mechanical resonators. The invention may also have suitable application with respect to thickness shear mode resonators, surface acoustic wave devices, pressure sensing devices, or ultrasonic transducers.

Examples of resonators and the manner of using them for sensing characteristics of a fluid are taught, for example, in U.S. Pat. Nos. 6,336,353 and 6,182,499, hereby expressly incorporated by reference.

Figure 1:
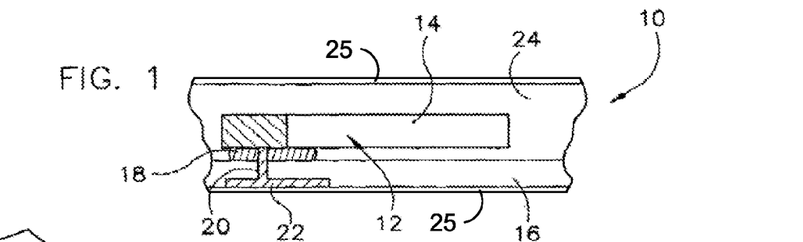
FIG. 1 is a side section view of a sensor of the present invention taken from the assembly of FIG. 2, wherein the sensor is enveloped by an optional Faraday cage.

FIG. 1 illustrates one example of an approach to packaging a resonator to form an assembly 10 in accordance with the present invention. The assembly 10 includes a resonator 12 having a free portion 14. A base platform 16 supports the resonator, by way of a suitable support 18, which may be formed as part of the base platform 16, added as a separate layer (e.g., a layer of dielectric material (e.g., a polymer, a ceramic or combination thereof), an adhesive such as an epoxy, or the like) or otherwise provided so that the free portion is spaced from the base platform over at least a portion of the length of the resonator. The assembly is preferably provided with a suitable structure adapted for receiving a signal. For example, in one embodiment, a conductive path 20 joins a contact 22 with the resonator (e.g., via a bonded or soldered joint with an electrode (not shown) associated with the resonator.

The structure of the conductive path and the contact is not critical, and it is possible to combine the two into a single structure. For example, it is possible that the conductive path may include a wire that is attached to an electrode of the resonator. Alternatively, using techniques common in the manufacture of semiconductor devices, a via may be formed in the base platform 16 and filled with a wire or conductive metal. The contact may be a wire. It may also be a conductive trace applied by a suitable metallization process (e.g., plating, physical vapor deposition, chemical vapor deposition, plasma deposition, coating, spraying, or the like). It may also be possible to laminate with or without an adhesive.

Though FIG. 1 depicts a structure by which the conductive path extends through a base, it will be appreciated that the invention is not so limited, and the path can extend through or around any wall, e.g., wall 24 of the assembly. The wall may be any suitable material, and preferably is a material similar in electrical characteristics to the material of the base platform 16 (e.g., a ceramic, a polymer or a combination thereof).

Figure 2:
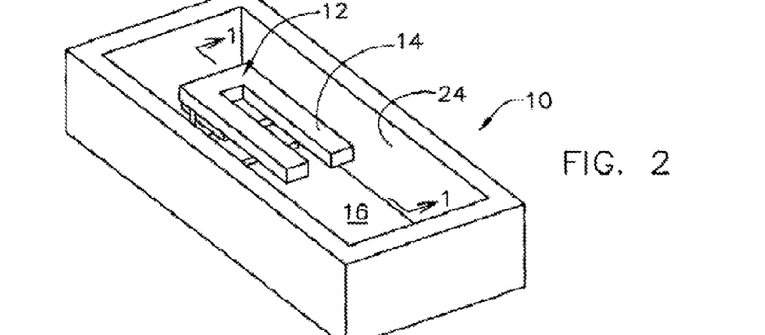
FIG. 2 is a perspective view of the sensor of FIG. 2 with the Faraday cage removed for clarity and depicting an illustrative housing configuration.

In FIG. 2, there is shown an example of a more complete housing structure in which the assembly 10 includes a plurality of walls 24 that substantially surround the resonator. Though shown as generally orthogonally disposed continuous, flat walls, of course, the invention is not so limiting, the walls can assume any shape as desired. They may include discontinuities, e.g., grooves, wells, apertures, slits, windows or some other surface irregularity. The walls may be curved, be configured as a polygon other than a rectangle, or combinations thereof. In a preferred embodiment, there is a cut-out defined in the housing structure so that at least the free end 14 of the resonator 12 is exposed. For example, as seen in FIG. 2, a top wall may be omitted from covering all or a portion of an upper portion of the housing structure to render at least a portion of the resonator exposed to ambient.

Figure 3A:
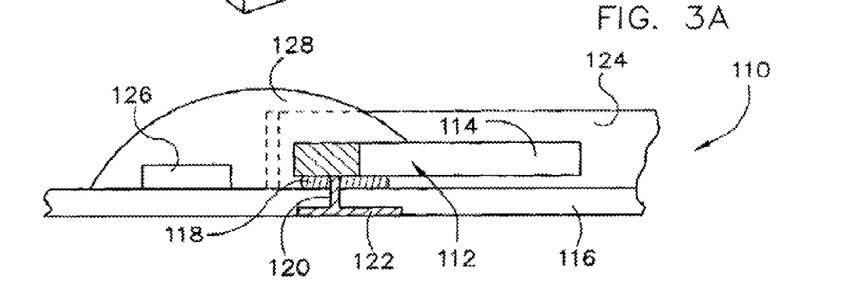
FIG. 3a-3b illustrate (with side sectional views) of a sensor of the present invention, shown coupled with another component and sharing a common platform, and also including an optional protective layer.

In another embodiment, an assembly including a resonator, such as the assembly in FIG. 1 may be combined with one or more other devices, and be carried together by a common platform. For example, it is contemplated that a resonator assembly may be packaged in combination with an ASIC and be carried by a common platform. With reference to FIG. 3a, there is shown one such example in which an assembly 110, including a resonator 112 having a free portion 114. A base platform 116 having a conductive path (which in this illustration is shown connected with a contact 122, but need not be, as described above) forms a surface upon which a support 118 may be disposed for the resonator 112. A wall 124 substantially surrounds the resonator 112, while at least partially exposing at least a portion of the resonator to ambient.

Figure 3B:
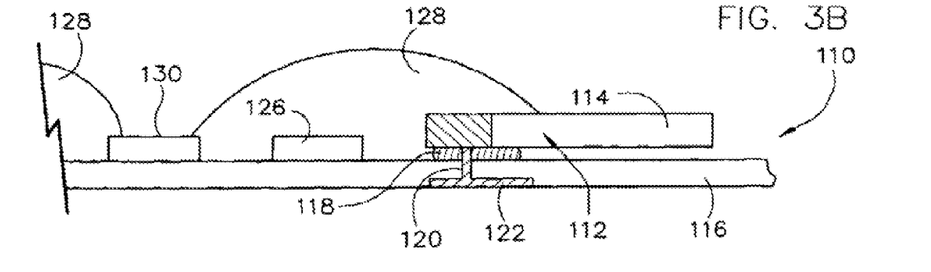

Also shown in FIG. 3a is an additional electronic component 126 (e.g., an ASIC). Shown in FIG. 3b is an additional electronic component 126 (e.g., an ASIC) and a secondary component 130 (e.g. a temperature sensor). Furthermore, the one or more devices on the platform may or may not be surrounded by a wall, which is shown in FIG. 3a, but absent from FIG. 3b.

Secondary components may be included on the common platform with the resonator. Besides temperature sensors (e.g. thermistors, RTDs, semiconductor bandgap or the like), other sensors may be utilized. Beside ASICs, other more general integrated circuits may be used. Also, integrated circuits that combine the functionality several devices or sensors may be used; for example, an integrated circuit that measures temperature as well operates the resonator may be suitable. A variety of passive and/or active components may be used to assist in the operation of the integrated circuit and/or resonator. For example, resistors (e.g. thin film resistors) and capacitors (e.g. ceramic capacitors) may be utilized as passive components. Examples of active components include amplifiers and/or filters. Also suitable for a use as a secondary component is a field programmable gate array. The conductive path may also be considered another device that may be included on the common platform with the resonator. In addition, a calibration unit may be utilized. Of course, various combinations of these other devices may also be used on a common platform with the resonator.

In a preferred embodiment, the electrical connection between the resonator and the integrated circuit as short as possible to help lessen signal distortions, interferences and parasitic effect that may affect measurement accuracy.

In both FIGS. 3a and 3b, there is also shown an optional protective layer 128 that may be applied to encapsulate at least a portion of the assembly. It will be appreciated that a similar protective layer may be employed over the various other alternative assemblies of the present invention as well, such as over the assembly 10 of FIG. 1. It is not only limited to the assembly 110 of FIGS. 3a and 3b.

The protective layer 128 may be any suitable protective layer. For example, it may be a coating that is sprayed, brushed or otherwise applied over the assembly; it may also include an overmolded plastic layer, a layer that is laminated, or combinations of two or more of coatings, overmolded layers, or laminated layers may also be employed.

It is found that in instances where it is desired to employ a protective layer, and the need remains to maintain the free portion of the resonator exposed to ambient, there is a need to selectively apply the protective layer to the assembly so that components needing protection from harsh environments will be coated, while still keeping the free portion of the resonator exposed. Also, the protective layer may be selectively applied to the one or more components on the assembly. For example, the protective layer may be selectively applied to the temperature sensor (item 130 in FIG. 3b) so that a portion of the temperature sensor remains exposed to ambient, while the protective layer fully coats the additional electronic component. In the alternative, the protective layer may fully coat the temperature sensor if it has a thermal conductivity.

In order to accomplish this, any of a number of suitable selective application techniques may be employed, such as the employment of a removable protective barrier to prevent protective layer materials from contacting the free portion of the resonator. The removable protective barrier is thus positioned over the assembly to block the portions of the assembly requiring the protective layer from the portions that do not require the layer. The protective layer is then applied and the barrier is removed.

The protective barrier may take any suitable configuration, but preferably is selected from a re-usable barrier or a consumable barrier. For example, it might be possible to employ a photoresist over a portion of the assembly, selectively remove portions thereof, apply the protective material and then remove remaining photoresist.

Figure 4:
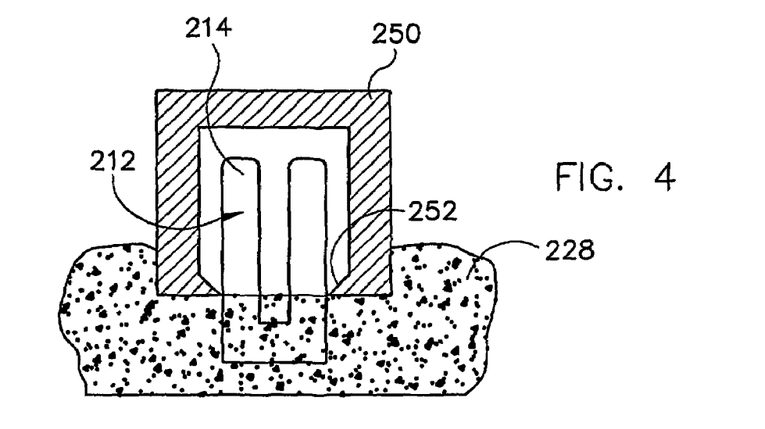
FIG. 4 is a top sectional view of an assembly in accordance with the present invention to illustrate the use of a removable barrier for temporary use while applying a protective layer to components of a sensor in accordance with the present invention.

FIG. 4 is a top sectional view of a resonator assembly 210 in which a re-usable barrier 250 is employed to surround a resonator 212 over a free portion 214, while a protective layer 228 is applied. The re-usable barrier may be any suitable material. However, preferably it is a relatively soft material that will not plastically deform the resonator if it contacts the resonator. It may include one or more knife edges 252, membranes, walls or the like at any suitable location (e.g., a knife edge seal along an inner periphery) to help sealingly surround the resonator during application of the protective layer. It should be appreciated that though the barrier of this embodiment may be re-usable, it need not be, particularly if to do so would compromise the quality of the resulting assembly. The re-usable barrier may be manually handled, or handled by an automated instrument for placement purposes. In a variation within this embodiment, one or a plurality of the barriers may be placed on a robot arm, which precisely brings the barrier (or barriers) into proper position relative to the resonator.

Figure 5A:
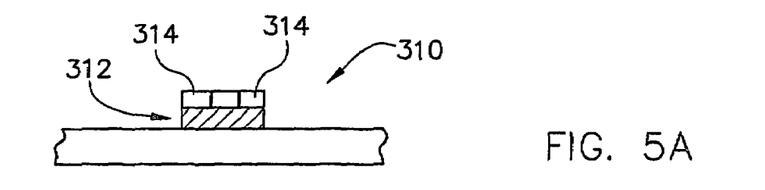
FIGS. 5a-5d illustrate (with side sectional views) a sequence of steps employed for applying a protective layer to components of a sensor in accordance with the present invention, in which a consumable barrier is employed.
Figure 5B:
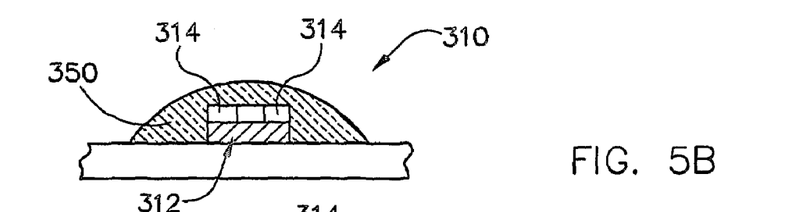
Figure 5C:
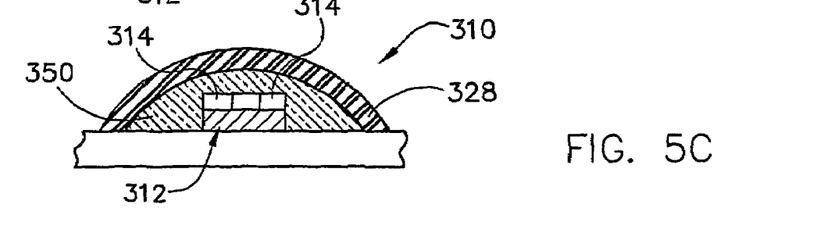
Figure 5D:
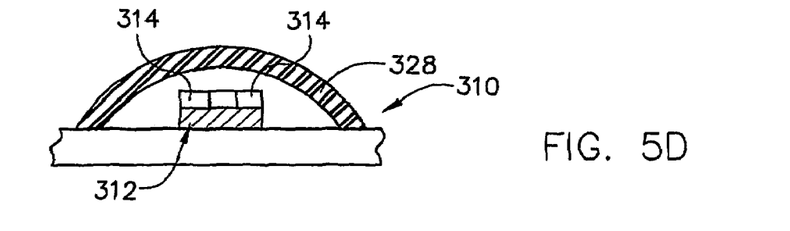

FIGS. 5a-5d illustrate a sequence of steps that may be employed, pursuant to which the removable protective barrier is a consumable barrier. In FIG. 5a there is shown an assembly 310, that includes a resonator 312 having tines defining a free portion 214. The resonator sits on a platform 318. In FIG. 5b, a consumable barrier layer 350 is applied over the resonator of the assembly of FIG. 5a. In the step depicted in FIG. 5c, a protective layer 328 is applied over the consumable barrier layer 350. In FIG. 5d, the consumable layer has been removed. Leaving the protective layer 328 in spaced relation from the resonator 312.

In yet another embodiment it may be possible to employ a hybrid approach to the approach of FIGS. 4 and 5a-5d. For example, a shell may be formed in situ to surround the resonator. Upon conclusion of application of the protective layer, the shell may be removed, such as by breaking it at a weakened region (e.g., a scored location).

It is preferable that any consumable barrier material that is used be relatively inert to the material of the resonator and any associated hardware so that no damage arises as a result of the method. In this regard, any of a number of different materials may be employed as the consumable layer. For example, the material of the consumable barrier may be a material that can be dissolved, decomposed or otherwise broken down into particles for removal from the volume of space between the resonator and any resulting protective layer. Thus, the consumable barrier material may be selected from polymers (synthetic, biological, thermoplastic, thermoset, or combinations thereof), starches, waxes, salts or other dissolvable crystals, low melting point metals, or another sacrificial material that is capable of withstanding in its solid state the processing conditions for applying the protective layer, and thereafter being removable from the assembly without physically deforming or otherwise contaminating the resonator.

Figure 6A:
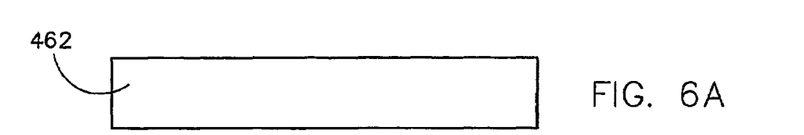
FIGS. 6a-6e illustrate (with side sectional views) a sequence of steps employed for assembling another sensor in accordance with the present invention.
Figure 6B:
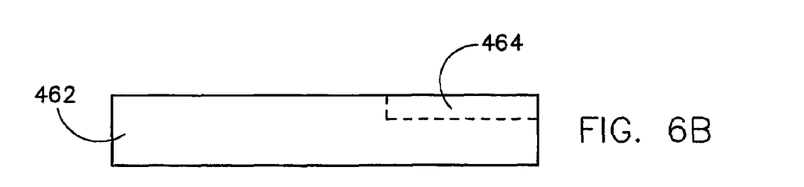

Turning now to the embodiment shown in FIGS. 6a-6e, there is shown another approach to the fabrication of an assembly 410 in accordance with the present invention. In the resulting assembly of this embodiment, a resonator 412 has a free portion 414 that extends away from a multi-layer holder 460. A first layer 462 is provided as shown in FIG. 6a. A trench 464 is formed in or on the first layer, as seen in FIG. 6b, using any suitable material removal or material build-up technique (e.g., etching, machining or the like for removal, or plating, physical vapor deposition, chemical vapor deposition, plasma deposition, coating, spraying, laminating with or without adhesive or the like, for build-up of spaced walls (not shown) for defining a trench).

Figure 6C:
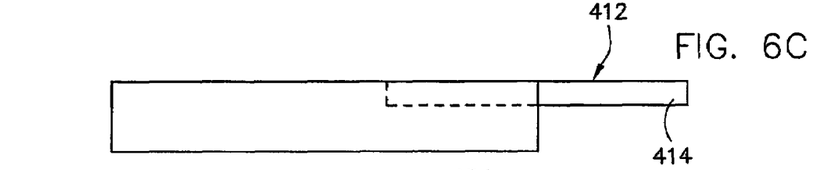
Figure 6D:
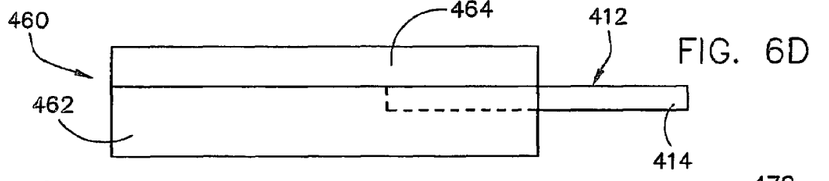
Figure 6E:
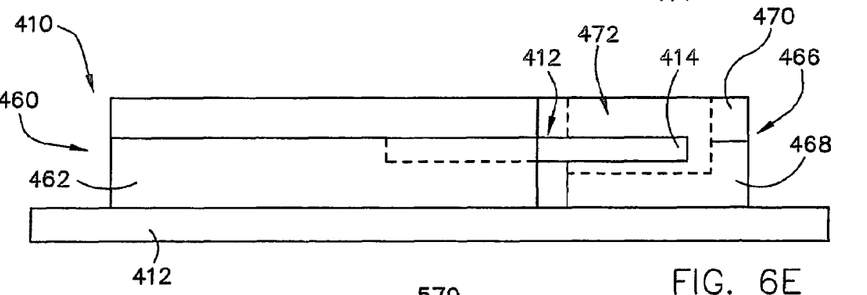

According to FIG. 6c, the resonator 412 is placed in the trench so that the free portion projects away from the first layer 462. Though it may be possible to mechanically fasten the resonator into the trench, or to adhesively bond it in place, FIG. 6d illustrates the placement of a second layer 464 over at least a portion of the first layer 462. The second layer may be fabricated on the first layer using any suitable technique such as attaching a preformed layer, such as by laminating with or without an adhesive, plating, physical vapor deposition, chemical vapor deposition, plasma deposition, coating, spraying, or the like. At this point the multi-layer holder 460 is complete and may be implemented into a further assembly. In FIG. 6e, there is shown one illustration of how the holder 460 may be incorporated into a further assembly, such as by attachment (e.g., via welding, adhesive bonding, wire bonding or the like). In the embodiment of FIG. 6e, a shield device 466 is fabricated to include a protective shield for the free portion of the resonator, while still maintaining the free portion 414 exposed for sensing. Thus, a lower portion 468 is assembled with an upper portion 470 about the resonator 412. Either or both of the lower portion 468 or the upper portion 470 may include a window that exposes the free end for sensing. The lower portion 468, the upper portion 470 or both may be pre-fabricated to include a suitable cavity 472 for receiving the resonator. The lower portion 468 and the upper portion 470 might also be fabricated separately, or as a single unit (e.g., as a molded plastic clam-shell type package). Though shown in FIG. 6e as being carried by a common platform 412, the holder 460 and shield device 466 may be maintained upon separate support surfaces.

Figure 7:
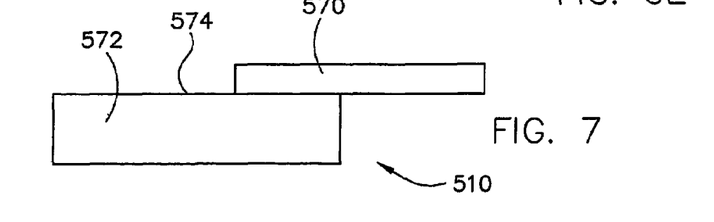
FIG. 7 illustrates a side view of a sensor of the present invention attached directly to an ASIC device.

FIG. 7 illustrates a side view of an assembly 510 in which a sensor 570 including a resonator is attached directly to another device, particularly an ASIC device 572. Though shown mounted on an outer surface 574 of the ASIC device 572, the sensor may penetrate through such an outer surface to an interior of the ASIC device. Attachment of the sensor to the ASIC device may be by any suitable technique, such as (without limitation) via welding, adhesive bonding, wire bonding or the like. The sensor 570 may simply include a resonator, or it may also be an assembly that includes additional packaging, such as that depicted in the various other embodiments as shown herein (e.g., as in FIGS. 1-6d and 8a-8d).

Figure 8A:
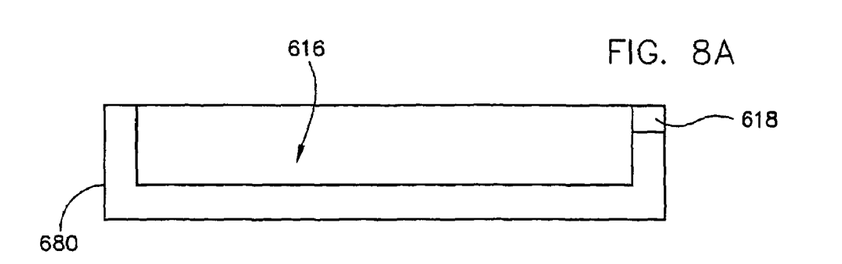
FIG. 8a-8d illustrate (with side sectional views) a sequence of steps employed for assembling yet another sensor in accordance with the present invention.

Turning now to FIGS. 8a-8d, there is shown yet another embodiment of the present invention in which an assembly 610 includes a first portion 680 and a second portion 682 that are attached together in a later-stage assembly step to enclose the assembly while leave a free portion 614 of resonator 612 exposed for sensing. It should be realized that a suitable shield device, such as shown in FIG. 6e may likewise be employed with the present assembly 612. As seen in FIG. 8a, preferably at least one (or both) of the first or second portions will be configured to include a well 616 for receiving components. Optionally, it may also have a suitable wall structure for defining a opening 618, through or on which the resonator 612 may be placed.

Figure 8B:
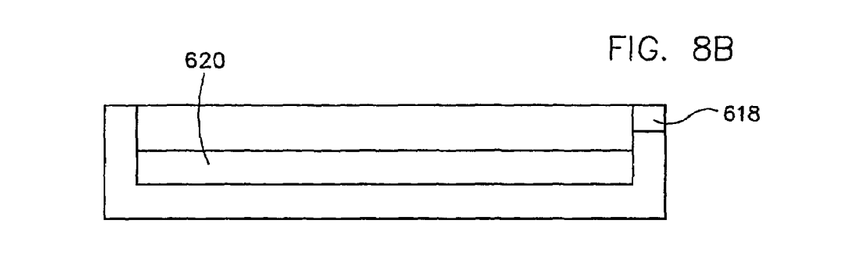
Figure 8C:
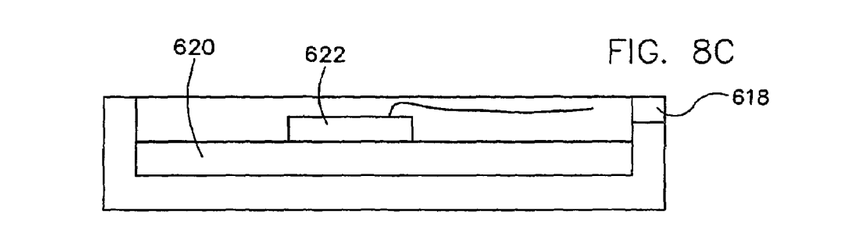
Figure 8D:
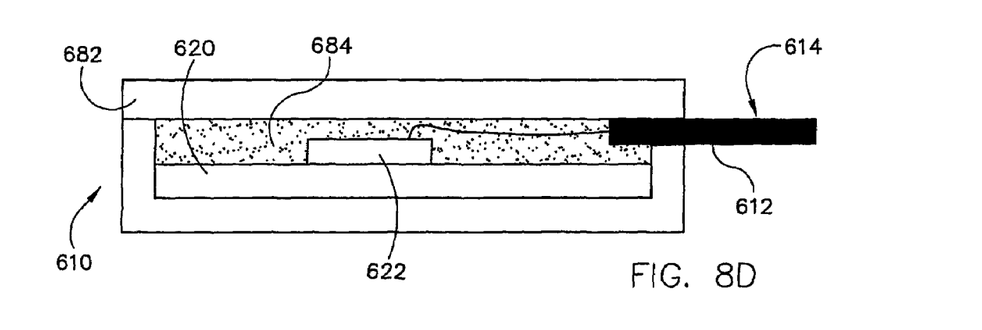

In FIG. 8b a first internal component 620 is placed in the well 616. In the step shown in FIG. 8c, a second internal component 622 (which may be pre-attached to or otherwise integrated into the first component, or omitted altogether) is placed in the well 616. Optionally, an electrical conductor 624 (e.g., wires, traces or otherwise) is attached to either or both of the first or second internal components. Pursuant to FIG. 8d, the resonator is connected with the electrical conductor, the second portion 682 is secured to the first portion (e.g., mechanically, by welding, by adhesive bonding or otherwise), and the well is optionally filled with an inert substance 684 (e.g., a gas, a gel, a liquid or otherwise).

Thereafter, the resulting assembly can be further handled (e.g., for placement on a common platform with an ASIC, for placement on an ASIC (as in FIG. 7) or otherwise), such as for attachment to a platform or to hardware for securing it in place in the intended sensing environment. It should be recognized that either of the first or second components might be an ASIC component.

As discussed in the above, in certain embodiments of the present invention it is preferable that a spacing be maintained between the free portion of any resonator and any adjacent structure. The amount of such spacing is not critical, and may vary depending upon the nature of the particular application. However, in the context of a preferred embodiment employing a tuning fork resonator, in order to help avoid the potential for electrical interference with the operation of the resonator, it is preferred that the spacing be at least one width of a tine of the tuning fork.

In any of the embodiments discussed herein, it is also possible that one or more additional structures are added to the assembly in order to help improve performance or functionality of the resulting device. For example, in one embodiment, the assembly includes a well or other suitable passage that is in direct fluid communication with the resonator and into which a calibration fluid can be introduced for the purpose of calibrating the sensor. It is also contemplated that the assembly may include a structure that substantially envelops the resonator for assisting to preserve electrical characteristics. For example, a wire mesh 25 or other like cover may be provided about the resonator as a Faraday cage, as illustrated schematically in Fig. 1. Other alternative structures may also be employed, such as the metallization of a region that at least partially surrounds the resonator. This can be employed in any of the above embodiments, including for example the embodiments of FIGS. 1-3 that employ a housing structure, or the embodiments of FIGS. 6a-6e and 8a-8d that might employ a shield device (which shield device, of course, may also be adapted for employment with a housing such as in FIGS. 1-3).

It should be appreciated that the functions that are described herein may be performed as part of a single integrated package, or they may be spread over a plurality of different components that may or may not be supported by a common platform.

Further, the present invention also contemplates the incorporation of one or more additional sensors apart from the resonator sensors described herein. For example, one embodiment contemplates the inclusion in an assembly of a sensor or other device for monitoring temperature, such as a thermistor, an RTD or other such temperature sensor (FIG. 3b). In this manner, it is contemplated that all of the data necessary for a calculation of viscosity, for example, can be obtained in a single assembly, which in turn can be interfaced with a suitable microprocessor.

It should be recognized that the present invention contemplates not only the methods employed for fabricating the assemblies of the present invention, but also the assemblies themselves, independent of the methods employed for fabrication. Thus the present invention contemplates sensor assemblies that include a resonator having a free portion with a sensing surface is incorporated onto a platform, wherein components of the sensor are physically shielded from harsh operating conditions, a spacing is maintained between the free portion of the resonator and the platform, and the sensing surface of the resonator is exposed for sensing.

The assemblies of the present invention may also be provided with suitable hardware for securing the assembly to another component, such as hardware for securing the assembly in an automotive vehicle engine or within a conduit, tank, or other structure for carrying a fluid.

It should also be recognized that even if not described in connection with one of the above embodiments, it is possible to combine steps from one of the embodiments shown with the other embodiments shown. For example, for each of the embodiments, it is contemplated that a protective layer may be applied over at least a portion of the resulting assemblies. This can be done by overmolding, coating or other art-disclosed techniques for protecting delicate hardware from the effects of intended operating conditions. Additionally, even if not shown, each of the embodiments might be further assembled onto a platform alone or with other components using art-disclosed attachment techniques (e.g., via welding, adhesive bonding, wire bonding or the like).

It should also be recognized that single layers shown herein may be split into additional layers to form more than the number of layers shown, or combined with other layers to form less than the number of layers shown. All such variations are contemplated within the scope of the present invention.

Further, the disclosure herein of a particular shape or orientation of a component is not intended as limiting. Though it is expected that many embodiments will employ relatively thin and flat structures, the components may also be fabricated or arranged so that the resulting structure has a curvature, a relatively thick profile, or a combination thereof (e.g., an assembly including a resonator and protective carrier structure that has a ratio of its largest to its smallest dimension of about 1:1 to about 4:1).

Finally, the omission herein in any particular embodiment of any discussion of electrical connections or other hardware for signally connecting the assemblies herein with other electronic components is not intended as limiting. It should be recognized that a variety of art-disclosed hardware configurations may be employed in each instance, such as the use of wires, traces, conductive metal filled vias, combinations thereof or the like.

As discussed above, the sensor may be a mechanical resonator, such as is disclosed for example in commonly owned, co-pending application entitled "Mechanical Resonators" (claiming benefit of U.S. provisional application No. 60/456, 292), incorporated by reference herein. The mechanical resonator has a resonator portion for resonating in a fluid and an electrical connection between the resonator portion and a source of a signal input. The resonator portion, the electrical connection or both include a base material and a performance-tuning material. The base material may include quartz, lithium niobate, zinc oxide, lead zirconate titanate (PZT), gallo-germanates (e.g., Langasite ($La_3Ga_5SiO_{14}$), Langanite, or Langatate), diomignite (lithium tetraborate), bismuth germanium oxide gallium phosphate, gallium nitride, aluminum nitride or combinations thereof. The performance-tuning material may include polymers, ceramics, metals, metal carbides or nitrides, diamond, diamond-like carbon, and combinations thereof.

The mechanical resonator may be connected to a measuring system that sends a variable frequency input signal, such as a sinusoidal wave, that sweeps over a predetermined frequency range, preferably less than about 100 kHz (e.g., in the 25-30 kHz range) for a tuning fork resonator and in a higher range for the TSM resonator. The resonator response over the frequency range is then monitored to determine selected physical and electrical properties of the fluid. Absolute values may be obtained if desired, as may relative, comparative or index values. Additionally, it is possible also that the system may be employed with determining whether a certain threshold criteria is met in the fluid being analyzed.

The hardware for the present measuring system may be any suitable hardware. It may include, for example, art-disclosed network analyzers, see, e.g., U.S. Pat. No. 6,336,353 (Matsiev, et al.)("Method And Apparatus For Characterizing Materials By Using A Mechanical Resonator"); and U.S. Pat. No. 6,182,499 (McFarland, et al.) and U.S. Pat. No. 7,302, 830, hereby incorporated by reference. The hardware might also be part of an application specific integrated circuit (ASIC), such as is disclosed for example in commonly owned U.S. Pat. No. 7,043,969, hereby incorporated by reference, as disclosed in commonly owned, U.S. Pat. No. 6,873,916, hereby incorporated by reference, as disclosed in co-owned, application entitled "Resonator Sensor Assembly" published as U.S. Pat. App. No. 20040250622 (now abandoned), as disclosed in co-owned application entitled "Environmental Control System Fluid Sensing System And Method" (International patent application no. US03/32983) or as disclosed in co-owned U.S. Pat. No. 7,210,332. All of the foregoing are hereby incorporated by reference.

Generally, the hardware for measuring system provides a versatile fluid sensing system. More specifically, the hardware provides a fluid sensing system for machines that rely upon the presence, condition or both of a fluid to maintain efficient operation, such as (without limitation) a synthetic or natural engine oil. In an automotive application, the user is provided with the ability to determine the actual condition (e.g. or the relative deviation of the state of the engine oil from its initial or virgin state) of the engine oil at any particular time, including during operation. Alternatively, in conjunction with assessing fluid condition, the hardware may also determine the amount of fluid remaining in a reserve of an assembly. This advantageously allows machine operators to extend the duration between fluid service events, while helping to assure continued operational integrity of a machine.

Any dynamic assembly that depends on fluids to operate (e.g., where friction and heat are of a concern), will benefit from hardware capable sensing the state of a fluid. For instance, the ability to dynamically monitor fluid condition, process data obtained from the monitoring, and report characteristics of the fluid to an interface or operator can have many applications. Assemblies that may benefit from the defined embodiments of the present invention are many, and can include without limitation, engines in general, automobiles, heavy machinery, military equipment, airplane parts, oil drilling, exploration and production well logging, oil refining, pipeline and quality control applications, marine transportation, sub-sea exploration and aerospace related equipment, or any other fluid containing application. In addition, contemplated methods include a step of assembling the hardware into a device that is incorporated into engines in general, automobiles, heavy machinery, military equipment, airplanes, oil drilling, exploration and production well logging equipment, oil refining, pipeline and quality control equipment, marine transportation equipment, sub-sea exploration and aerospace related equipment, or any other equipment that utilizes fluids for operations.

In the automotive field, numerous components require lubrication, which is not limited to engine oil. For example, other automotive components may include the transmission, the transfer case, the differential, etc. Still further, the sensing system may further be used to determined the quality and amount of other fluids which are not necessarily used predominantly as a lubricant, including: brake fluids, steering fluids, antifreeze fluids, refrigerant fluids, windshield washer fluids, or any other fluid located in an automotive system.

In one embodiment of suitable hardware, an oil sensing system is used to determine the component characteristics and amount of engine oil. In an automotive application, the oil sensing system will provide a user, at a minimum, with a warning as to the need to change the oil (such as owing to the presence of contaminants, a breakdown or loss of useful ingredients or otherwise). In such an application, the warning is essentially informing the user of the automobile that the engine oil has reaches a quality level or condition that is lower than that recommend by the automobile's manufacturer (or set by the oil manufacturer).

The fluid sensing system preferably uses a mechanical resonator as the fluid sensor in accordance with the present invention. The mechanical resonator is at least partially contained in the fluid under-test. To monitor the condition of the fluid under-test (i.e., engine oil), the mechanical resonator is provided with electrical energy through a frequency generator. The frequency generator is designed to apply a frequency signal (to the mechanical resonator) that is swept over a predetermined frequency range. Electronics are then used to detect the response signal from the mechanical resonator and process the signal to ascertain characteristics of the fluid under-test. In an embodiment of the fluid sensing system, the electronics are provided in the form of an application specific integrated circuit (ASIC). In addition, the hardware might also be part of or include a field programmable gate array (FPGA).

In the foregoing description, numerous specific details are set forth in order to provide a thorough understanding of the fluid sensing system, hardware and mechanical resonator that may be used with the present invention. It will be apparent, however, to one skilled in the art that the present invention may be practiced without some or all of these specific details. In other instances, well known process steps have not been described in detail in order not to unnecessarily obscure the present invention.

The manner of operating the resonators and sensors of the present invention may vary. In one embodiment, the sensor is operated continuously. In another, it may be intermittently operated. It is possible that the sensor may be operated only in preselected conditions, such as prior to starting vehicle operation, upon starting vehicle operation, during vehicle operation upon concluding vehicle operation, while the vehicle travels at a substantially constant velocity, while the vehicle accelerates or decelerates, or otherwise.

It should be understood that various alternatives to the embodiments of the invention described herein may be employed in practicing the invention. It is intended that the following claims define the scope of the invention and that the methods and apparatus within the scope of these claims and their equivalents be covered thereby. To the extent that the particular combinations of steps and materials covered by the following claims are not disclosed in the specification, the combinations of steps and materials are incorporated by reference into the specification.

What is claimed is:

1. A fluid sensor package comprising:
    a tuning fork resonator on a platform, the tuning fork resonator comprising tines, each tine having one or more surfaces, each tine further comprising an electrode, and a piezoelectric material selected from the group consisting of quartz and lithium niobate, wherein the electrodes are positioned to apply electrical fields to the piezoelectric materials in the respective tines to move said surfaces of the tines relative to the platform to displace a fluid in contact with the tines,
    an application specific integrated circuit (ASIC) on the platform, the ASIC being in electrical communication with the electrode of each tine for providing stimulus to the tuning fork resonator and for receiving a response signal from the tuning fork resonator, the ASIC being operable to determine one or more characteristics of the fluid from the response signal, and
    a secondary component on the platform and spaced from the ASIC, the secondary component being selected from the group consisting of a temperature sensor, a field programmable gate array, a calibration unit, a conductive path, a resistor, a capacitor, an amplifier, a filter, and combinations of two or more thereof.

2. The fluid sensor package of claim 1 wherein the ASIC comprises a temperature sensor, or wherein the secondary component comprises a temperature sensor.

3. The fluid sensor package of claim 1 wherein the tuning fork resonator is capable of operating at temperatures between −60° C. and 300° C.

4. The fluid sensor package of claim 1 wherein the tuning fork resonator is capable of operating at temperatures between −40° C. and 170° C.

5. The fluid sensor package of claim 1 wherein ASIC is operable to determine a viscosity of the fluid and to determine a density of the fluid independent of said viscosity using the response signal from the tuning fork resonator.

6. The fluid sensor package of claim 1 wherein the package is installed in apparatus selected from the group consisting of an engine, an automobile, an airplane, production well logging equipment, and a pipeline.

7. The fluid sensor package of claim 1 further comprising a Faraday cage positioned to envelop the tuning fork resonator.

8. The fluid sensor package of claim 1 wherein the package is installed in a system selected from the group consisting of an engine, a transmission, a transfer case, a differential, a brake system, a steering system, an antifreeze system, a heating and cooling system, and a washer system.

9. The fluid sensor package of claim 1 wherein the package is adapted for use in lubricants, brake fluids, steering fluids, antifreeze fluids, refrigerant fluids, and washer fluids.

10. The fluid sensor package of claim 1 wherein the secondary component is in electrical communication with the ASIC.

11. The fluid sensor package of claim 1, further comprising a housing spaced from the tines.

12. The fluid sensor package of claim 11 wherein the housing includes a plurality of walls that substantially surround the tuning fork resonator while maintaining exposure of said surfaces of the tines to the fluid.

13. The fluid sensor package of claim 1 further comprising a protective layer covering a portion of the tuning fork resonator and a portion of the platform.

14. The fluid sensor package of claim 13 wherein the protective layer covers, partially or completely, the ASIC or the secondary component.

15. The fluid sensor package of claim 1 wherein the tuning fork resonator on the platform has a length smaller than 5 mm.

16. The fluid sensor package of claim 15 wherein the tuning fork resonator on the platform has a length smaller than 1 mm.

17. The fluid sensor package of claim 1 wherein the package has a volume of about less than 15 cm$^3$.

18. The fluid sensor package of claim 17 wherein the package has a volume of about less than about 10 cm$^3$.

19. The fluid sensor package of claim 1 wherein the package has a footprint of less than about 40 cm$^2$.

20. The fluid sensor package of claim 19, wherein the package has a footprint of about less than about 20 cm$^2$.

* * * * *